United States Patent
Mazzarolo et al.

(10) Patent No.: US 8,938,820 B2
(45) Date of Patent: Jan. 27, 2015

(54) PROTECTING DEVICE FOR THE NECK

(75) Inventors: Giovanni Mazzarolo, Coste di Maser (IT); Coliln Ballantyne, Caselle d-Asolo (IT)

(73) Assignee: Alpinestars Research SRL, Coste di Maser (IT)

( * ) Notice: Subject to any disclaimer, the term of this patent is extended or adjusted under 35 U.S.C. 154(b) by 979 days.

(21) Appl. No.: 12/990,584

(22) PCT Filed: May 2, 2008

(86) PCT No.: PCT/IT2008/000300
§ 371 (c)(1),
(2), (4) Date: Nov. 1, 2010

(87) PCT Pub. No.: WO2009/133579
PCT Pub. Date: Nov. 5, 2009

(65) Prior Publication Data
US 2011/0041240 A1    Feb. 24, 2011

(51) Int. Cl.
*A41D 13/00*  (2006.01)
*A61F 5/055*  (2006.01)
*A41D 13/05*  (2006.01)
*A42B 3/04*   (2006.01)

(52) U.S. Cl.
CPC ............ *A61F 5/055* (2013.01); *A41D 13/0512* (2013.01); *A42B 3/0473* (2013.01)
USPC .......................................................... 2/468

(58) Field of Classification Search
CPC .................... A41D 13/0512; A41D 2600/102; A42B 3/0473; A61F 5/055; A63B 71/1291
USPC ............ 2/455, 459, 460, 461, 462, 463, 410, 2/411, 412, 413, 414, 415, 421, 468, 44, 2/45, 129, 265, 266, 267, 268
See application file for complete search history.

(56) References Cited

U.S. PATENT DOCUMENTS

| 2,820,455 A |   | 1/1958 | Hall |
| 3,076,206 A |   | 2/1963 | Shaw et al. |
| 3,189,917 A | * | 6/1965 | Sims ................................ 2/415 |
| 3,202,307 A |   | 8/1965 | Rainer et al. |

(Continued)

FOREIGN PATENT DOCUMENTS

| DE | 27 17 712 A1 | 10/1978 |
| DE | 31 36 466 A1 | 4/1983 |

(Continued)

OTHER PUBLICATIONS

"PCT International Search Report dated Dec. 12, 2008 for PCT/IT2008/000300, from which the instant application is based," 4 pgs.

(Continued)

*Primary Examiner* — Khoa Huynh
*Assistant Examiner* — Anna Kinsaul
(74) *Attorney, Agent, or Firm* — Fredrikson & Byron, P.A.

(57) ABSTRACT

A protective device for the neck, such as a neck brace, with a substantially rigid closed structure around the neck and adapted to sit on the user's torso includes means for temporarily changing the device's shape so as to reduce the natural gap between the upper brace surface and the lower rim of the helmet, thereby creating a supplementary transmission path for compressive forces exerted upon the device towards the torso.

16 Claims, 1 Drawing Sheet

(56) References Cited

U.S. PATENT DOCUMENTS

| | | |
|---|---|---|
| 3,477,425 A | 11/1969 | Grassi |
| 3,495,272 A | 2/1970 | Tempelhof |
| 3,765,412 A | 10/1973 | Ommaya et al. |
| 3,849,801 A | 11/1974 | Holt et al. |
| 3,855,631 A | 12/1974 | Ettinger |
| 3,858,241 A | 1/1975 | Durand et al. |
| 3,878,561 A | 4/1975 | Winiecki |
| 4,274,161 A | 6/1981 | Littler |
| 4,319,362 A | 3/1982 | Ettinger |
| 4,422,454 A | 12/1983 | English |
| 4,441,211 A | 4/1984 | Donzis |
| 4,449,251 A | 5/1984 | Gauthier |
| 4,501,023 A | 2/1985 | Bilberry |
| 4,502,471 A | 3/1985 | Owens |
| 4,554,681 A | 11/1985 | Kirkland |
| 4,675,912 A | 6/1987 | Kirkland |
| 4,821,339 A | 4/1989 | Fair |
| 4,854,306 A | 8/1989 | Pujals, Jr. |
| 4,989,265 A | 2/1991 | Nipper et al. |
| 4,996,720 A | 3/1991 | Fair |
| 5,003,968 A | 4/1991 | Mars |
| 5,039,035 A | 8/1991 | Fitzpatrick |
| 5,133,084 A | 7/1992 | Martin |
| 5,230,698 A | 7/1993 | Garth |
| 5,411,471 A | 5/1995 | Terrazas |
| 5,437,613 A | 8/1995 | Reggio et al. |
| 5,517,699 A | 5/1996 | Abraham, II |
| 5,531,669 A | 7/1996 | Varnau |
| 5,546,609 A | 8/1996 | Rush, III |
| 5,590,826 A | 1/1997 | Endo |
| 6,058,517 A | 5/2000 | Hartunian |
| 6,067,665 A | 5/2000 | DePalma et al. |
| 6,494,854 B1 | 12/2002 | Visness |
| 6,729,643 B1 | 5/2004 | Bassick et al. |
| 7,017,194 B2 | 3/2006 | Schroth et al. |
| 7,041,073 B1 | 5/2006 | Patron |
| 7,329,230 B2 | 2/2008 | Mazzarolo |
| 7,371,221 B1 | 5/2008 | Baker |
| 2004/0167448 A1 | 8/2004 | Heffez |
| 2007/0010771 A1 | 1/2007 | Leatt |
| 2007/0106194 A1 | 5/2007 | Pickering et al. |
| 2007/0281125 A1 | 12/2007 | Moore et al. |
| 2010/0056968 A1 | 3/2010 | Mazzarolo |
| 2010/0121238 A1 | 5/2010 | Mazzarolo |
| 2010/0235973 A1 | 9/2010 | Mazzarolo |
| 2010/0251468 A1 | 10/2010 | Mazzarolo |
| 2010/0263112 A1 | 10/2010 | Mazzarolo |
| 2011/0004980 A1 | 1/2011 | Leatt et al. |

FOREIGN PATENT DOCUMENTS

| | | | |
|---|---|---|---|
| DE | 295 21 373 U1 | 4/1997 | |
| DE | 195 45 299 A1 | 6/1997 | |
| DE | 200 06 084 U1 | 8/2001 | |
| EP | 0023115 | 1/1981 | |
| EP | 0043990 A1 | 1/1982 | |
| FR | 2534115 | 4/1984 | |
| FR | 2700746 A | 7/1994 | |
| FR | 2719747 A | 11/1995 | |
| GB | 2 126 485 A | 3/1984 | |
| JP | 5747235 | 3/1982 | |
| JP | 200014686 | 1/2000 | |
| SL | 9600306 A | 4/1998 | |
| WO | 9809545 A1 | 3/1998 | |
| WO | 9938401 A1 | 8/1999 | |
| WO | 0125088 A | 4/2001 | |
| WO | 02089620 A1 | 11/2002 | |
| WO | 03077793 A2 | 9/2003 | |
| WO | 03092561 A | 11/2003 | |
| WO | 2005051251 | 6/2005 | |
| WO | 2005107658 | 11/2005 | |
| WO | WO 2007050024 A1 * | 5/2007 | ........... A41D 13/018 |
| WO | 2008050307 A1 | 5/2008 | |

OTHER PUBLICATIONS

"PCT Written Opinion dated Dec. 12, 2008 for PCT/IT2008/000300, from which the instant application is based," 5 pgs.

"PCT International Preliminary Report on Patentability dated Mar. 2, 2010 for PCT/IT2008/000300, from which the instant application is based," 6 pgs.

English-language Abstract FR2534115 (Nolan SPA), Pub: Apr. 13, 1984.

English-language Abstract FR2700746 (Schegerin), Pub: Jul. 29, 1994.

English-language Abstract FR2719747 (Streiff Motorsport), Pub: Nov. 17, 1995.

* cited by examiner

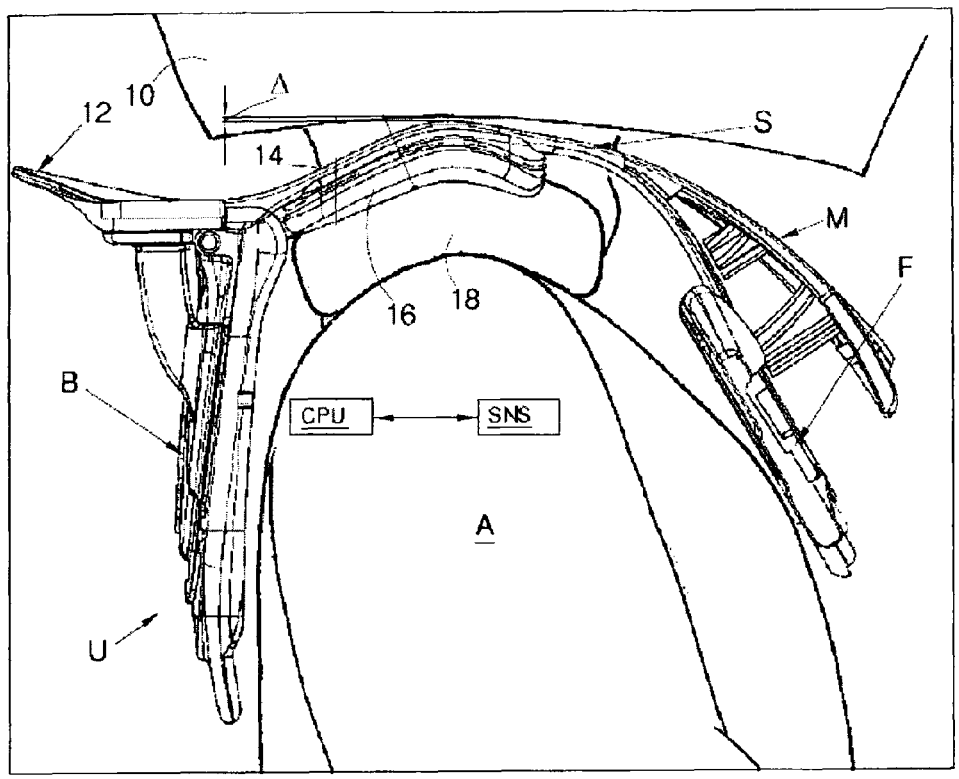
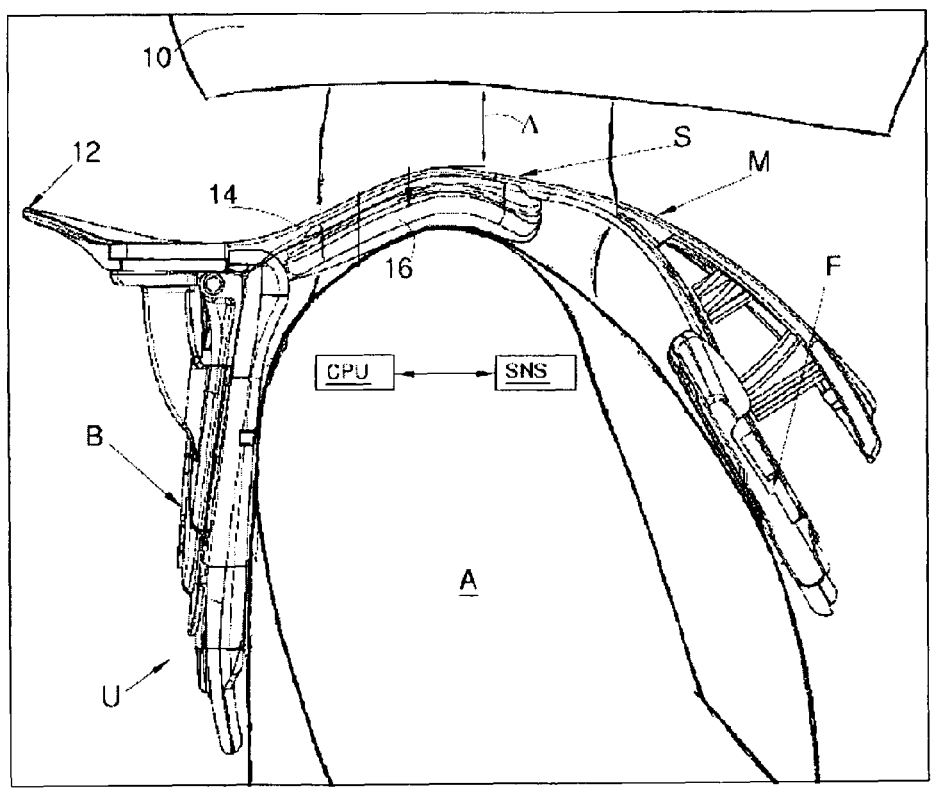

PROTECTING DEVICE FOR THE NECK

RELATED APPLICATIONS

This application is a U.S. 371 national stage entry of International Application No. PCT/IT2008/000300, filed May 2, 2008, the teachings of which are incorporated herein by reference.

BACKGROUND

It is known that devices exist which are designed to reduce the chances of sustaining a catastrophic neck injury in some, but not all, riding situations.

These devices are worn around the neck of the rider and interacts with the underside rim of the rider's helmet in order to provide an alternative load path for compressive forces. When used correctly the device can reduce the magnitude of these forces and helps avoid the type of injury that riders fear above all others: damaging their spinal cord.

An example of such a device is shown in WO2005051251 in the name of Leatt. Here the protection is just a round, quite rigid collar which may be divaricated and then arranged around the neck. It has a fixed structure once worn.

Applicant's studies have shown that a key reason why riders break their neck is that when they land upside down their head is squashed into the body and the neck is often damaged due to the compression. If one lands directly on top of his head there is a very high probability that the neck could break. However if the impact occurs to the side of the head, the chance of breaking reduces. This is because the amount of force going through your neck is reduced, i.e. less force is channeled through your neck.

Injury severity is mainly influenced by the height of the fall and not the speed over the ground. Falling on the top of your head from a height greater than 55 cm (1' 10") can be enough to break your neck—even if you are stopped.

Thus, the only real way to avoid breaking your neck is to limit the overall compression and one way of doing this is to offer an alternative load path around the neck. However up until now, the biggest flaw in this method of protection is that in order to allow some movement of the head (essential when riding a motorcycle) a gap must exist between the rim of the helmet and the upper surface of the device. The unfortunate fact is that this gap prevents the best load transfer and thus limits the effectiveness. The real benefit comes when there is contact (or a very small gap) between the brace and helmet at the time of impact, something that does not happen automatically.

BRIEF SUMMARY OF EMBODIMENTS OF THE INVENTION

It is therefore an object of the present invention to provide a protective device for the neck, which lessens the problem cited above and has improved effectiveness.

The object is achieved by a protective device for the neck, preferably a neck brace, with a substantially rigid closed structure around the neck and adapted to sit on the user's torso, characterized by the inclusion of means for temporarily changing or modifying the device's shape so as to reduce the gap between the device and the torso, thereby deliberately creating a supplementary transmission path for compressive forces exerted upon the device towards the torso.

To receive optimal protection the helmet should be in contact with the brace before impact. As discussed above, this does not happen often—and generally not without the rider making a deliberate effort to do this.

Thus this invention attempts to provide the best of both worlds—the most free head movement when there is no accident—but little or no gap between the head and shoulders when there is an accident. This gives the most comfort to the rider when riding, and the most protection in the event of a crash—as it attempts to guarantee that the helmet and brace will be in contact at the time of impact.

Appropriate sensing means detect the impact/danger condition and fire said means for temporarily changing. Preferably an electronic circuit with known sensors (accelerometers, gyroscopes, earth magnetic field sensors, etc.) is used. Note that a further possible embodiment of the sensing system is to trigger the system when only the neck is at risk. This means that the system would discriminate and not deploy in minor crashes where the risk is perceived as low.

It is important to note that the device of the invention does not work in the same way as a back protector or knee guard. These devices contain materials which are designed to absorb energy, which they do by deforming and compressing. The device of the invention works on the opposite principle: it has to transfer the load with the minimum amount of compression, and every millimeter counts. For example going from an 18 mm to a 23 mm gap could be the difference between a catastrophic neck injury or not.

Favorite variants for the invention, to be used alone or in combination, consist of:

- the means for temporarily changing comprising deployable means placed on the surface of the device facing the torso when in use and able, after deployment, to reduce the gap between the brace and the torso, more specifically by inflating one or more inflatable chambers. The invention may exploit known and reliable inflation technologies to provide said means in a very light, compact, quickly responsive arrangement. Of course speed is a key factor;
- said means for temporarily changing being adapted to generate a supplementary contact structure between the device and the torso having a stiffness equal to, or grater than, 30 N/mm. This value has proved to be satisfactory to reduce compressive loads;
- the means for temporarily changing being designed to generate a supplementary lifting of the brace structure towards the head. This can be adjustable depending on the size of the user but is typically between 40-80 mm in height. Note that maintaining symmetry around the neck for the changed shape is a further benefit and assures optimal load transfer to the torso: thus the means for temporarily changing are designed to enlarge the means of load transfer under the brace such that the gap between the helmet and brace is minimized or eliminated.
- the means for temporarily changing being designed to raise the neck brace from the torso by at least 60 mm with respect to its position held before shape modification. This "delta" of elevation has proved to be good with most helmets;
- means for freezing, heating the surface of the means for temporarily changing. During reshaping said means for changing could reach, depending on the embodiment chosen, high or low temperatures unpleasant or dangerous for the user. This prevents discomfort or injury. Preferably an insulated chamber material is used;
- means for removing on user's command the means for temporarily changing. This helps the rider to gain a correct and not dangerous posture after the incident, letting him to ride again without a shape-changed neck brace. Preferably, means for removal are designed so as to be acted upon only after the means for temporarily changing have changed the brace's shape, to prevent false triggering.

Neck brace comprises an upper continuous flat surface which is optimized to interface with the underside of a crash helmet. This means that the said surface curves in a gradual 'n' shape over the shoulders, but is completely smooth as to prevent any features on the rim of the helmet engaging. It is important that in the event of compressive injury only the compression is prevented and the head is free to move in all other directions; the smooth surface helps ensure this.

BRIEF DESCRIPTIONS OF DRAWINGS

These and other aspects of the invention will be apparent from the following detailed description of an example, whose drawings are so organized:

FIG. 1 illustrates a side view of a neck brace in idle position;

FIG. 2 illustrates a side view of a neck brace after a change in shape thereof occurred.

DETAILED DESCRIPTION OF EMBODIMENTS OF THE INVENTION

A user U with an helmet 10, e.g. a motorcyclist, is partly shown in the figures wearing on his torso and arm A a neck brace 12 composed by a rear part B, abutting on the back, a front part F, abutting on the chest, and an annular part M between them forming a ring around the neck.

The neck brace 12 is symmetrical with respect to a vertical axis (its right part is the same as the left). The annular part M is made of two curved, flat segments 14 (one visible in FIGS. 1 and 2) offering a flat, substantially horizontal surface S towards the helmet 10. When the neck brace 12 is worn normally, between the helmet 10 and the surface S there remains a void, vertical space or gap Δ of approximately 55 mm.

Under each of the segments 14 a padding 16 is arranged, which normally rests upon the user's shoulders. Inside, or on the side of, each padding 16 there is an inflatable chamber 18 (structured like a common air-bag) whose volume is controlled by an electronic and processing unit PU. The unit PU is connected with sensors stored in the rear of the unit on component 'B' or may be wirelessly linked to other sensors on spread on the vehicle and/or the suit of the user U, generically depicted as a block SNS, able to detect, and measure the gravity of, a sudden accident to the user U. Suitable and known algorithms can be used for this to program the unit PU.

In operation, the unit PU constantly controls via the sensors SNS the status of the user U (position and motion) and/or the riding conditions. When it detects a collision, an impact, or a probable violent unseating of the rider U from the vehicle, the unit PU commands the firing (inflation) of the chamber 18, which expands under the segments 14 (see FIG. 2). This increased volume has the consequence of changing the shape of the neck brace 12 raising it with respect to its (idle) position in FIG. 1, thereby reducing the distance Δ. The inflation occurs in approximately 40-80 ms, thus we can presume that the helmet 10 will collide sooner with the surface S before a real damage happens to the user's neck. The reduced Δ (nearly 60-80 mm) allows the helmet 10 to contact the neck brace 12 after a shorter time, and through this anticipated contact the helmet 10 can discharge the external impact forces (if any) imparted on it through the transmission path helmet 10->surface S->chamber 18->torso (see arrow F in FIG. 2).

It is possible that the chamber 18 may deform slightly during impact, but it must not collapse during the force transfer, i.e. it must be of adequate stiffness (a proper internal air pressure is sufficient).

The invention claimed is:

1. A neck brace comprising:
   a substantially rigid structure configured to be positioned around a neck of a user and to sit on a torso of the user, said structure leaving during normal wearing a natural gap between an upper surface of the structure and a lower rim of a helmet worn by the user;
   means for temporarily changing a shape of the neck brace comprising one or more inflatable chambers placed on a lower surface of the structure facing, when in use, the torso of the user, said one or more inflatable chambers configured to selectively expand under the structure so as to raise the structure from the torso of the user and move the structure from a first position to a second position;
   sensing means that detects an impact/danger condition; and
   a control unit that commands inflation of said one or more inflatable chambers when the impact/danger condition is detected, thereby raising the structure from the first position to the second position and reducing or eliminating the natural gap between the upper surface of the structure and the lower rim of the helmet, and creating a supplementary transmission path for compressive forces exerted upon the neck brace towards the user's torso,
   wherein the upper surface of the structure, suitable for being in contact with the lower rim of the helmet, is a rigid surface.

2. The neck brace according to claim 1, wherein the upper surface of the structure curves in a gradual "n" shape over shoulders of the user, said upper surface being completely smooth.

3. The neck brace according to claim 1, wherein said one or more inflatable chambers are adapted to generate a supplementary contact structure between the structure and the user's torso having a stiffness equal to, or greater than, 30 N/mm.

4. The neck brace according to claim 1, wherein said one or more inflatable chambers are designed to raise the structure from the user's torso by at least 60 mm with respect to the neck brace's position held before said changing.

5. The neck brace according to claim 1, comprising means for freezing or heating a surface of said one or more inflatable chambers.

6. The neck brace according to claim 5, wherein the means for freezing or heating the surface of said one or more inflatable chambers comprise an insulated chamber material.

7. The neck brace according to claim 1, further comprising means, on command from the user, for removing said one or more inflatable chambers after use of said one or more inflatable chambers.

8. The neck brace according to claim 7, wherein the means for removal are designed so as to be acted upon only after said one or more inflatable chambers have raised the structure from the torso of the user.

9. The neck brace according to claim 1, wherein said one or more inflatable chambers are designed to create two supplementary transmission paths for compressive forces, each arranged symmetrically around the user's neck.

10. The neck brace according to claim 1, wherein the sensing means are stored in a rear of the structure.

11. The neck brace according to claim 1, wherein the sensing means are selected from the group consisting of: accelerometers, gyroscopes, and earth magnetic field sensors.

12. The neck brace according to claim 1, wherein said one or more inflatable chambers are situated at a base of the user's neck when the structure is in the first position.

13. The neck brace according to claim 1, wherein said one or more inflatable chambers permit movement of a user's head when the structure is in the second position.

14. The neck brace according to claim 1, wherein said one or more inflatable chambers permit side-to-side movement of a user's head both when the structure is in the first position and when the structure is in the second position.

15. The neck brace according to claim 14, wherein permitted movement of the user's head when the structure is in the first position results from the natural gap.

16. The neck brace according to claim 14, wherein permitted movement of the user's head when the structure is in the second position results from the upper surface of the structure being smooth.

* * * * *